United States Patent [19]

Penrod et al.

[11] 4,136,449
[45] Jan. 30, 1979

[54] ADJUSTABLE DENTAL BRIDGE FIRING STAND

[76] Inventors: Evan P. Penrod, 1676 E. 8850 South; Charles K. West, 256 E. 9585 South, both of Sandy, Utah 84070

[21] Appl. No.: 758,595

[22] Filed: Jan. 12, 1977

[51] Int. Cl.² ............................................ A61C 13/00
[52] U.S. Cl. ..................................... 32/2; 32/40 R; 432/258
[58] Field of Search ............... 32/2, 1, 40 R; 164/376, 164/DIG. 4; 269/321 W, 296; 249/16, 17, 18; 432/258, 259; 264/59, 17

[56] References Cited

U.S. PATENT DOCUMENTS

| | | | |
|---|---|---|---|
| 1,530,479 | 3/1925 | Carlson | 432/259 |
| 1,733,895 | 10/1929 | Matteson, Jr. | 264/17 |
| 1,963,242 | 6/1934 | Nelson | 432/259 |
| 2,030,707 | 2/1936 | McLean | 432/259 |
| 2,881,502 | 4/1959 | Dopera | 248/346 |
| 2,910,962 | 11/1959 | Appleton | 432/259 |
| 3,861,867 | 1/1975 | Ouhl | 432/258 |
| 3,885,313 | 5/1975 | Kikuchi et al. | 32/40 R |
| 3,936,937 | 2/1976 | Gordon | 32/1 |
| 3,958,924 | 5/1976 | Egenolf et al. | 32/1 |

FOREIGN PATENT DOCUMENTS

| | | | |
|---|---|---|---|
| 684400 | 11/1939 | Fed. Rep. of Germany | 432/259 |
| 348245 | 5/1931 | United Kingdom | 432/259 |
| 406809 | 3/1934 | United Kingdom | 432/259 |

Primary Examiner—Russell R. Kinsey
Assistant Examiner—John J. Wilson
Attorney, Agent, or Firm—K. S. Cornaby

[57] ABSTRACT

An Adjustable Dental Bridge Firing Stand that is adjustable to hold all sizes, shapes and types of dental bridge frameworks; which need to be moved, placed in and held in a dental porcelain oven, or to be held during the various stages of firing the applied porcelain to complete a finished dental bridge.

4 Claims, 16 Drawing Figures

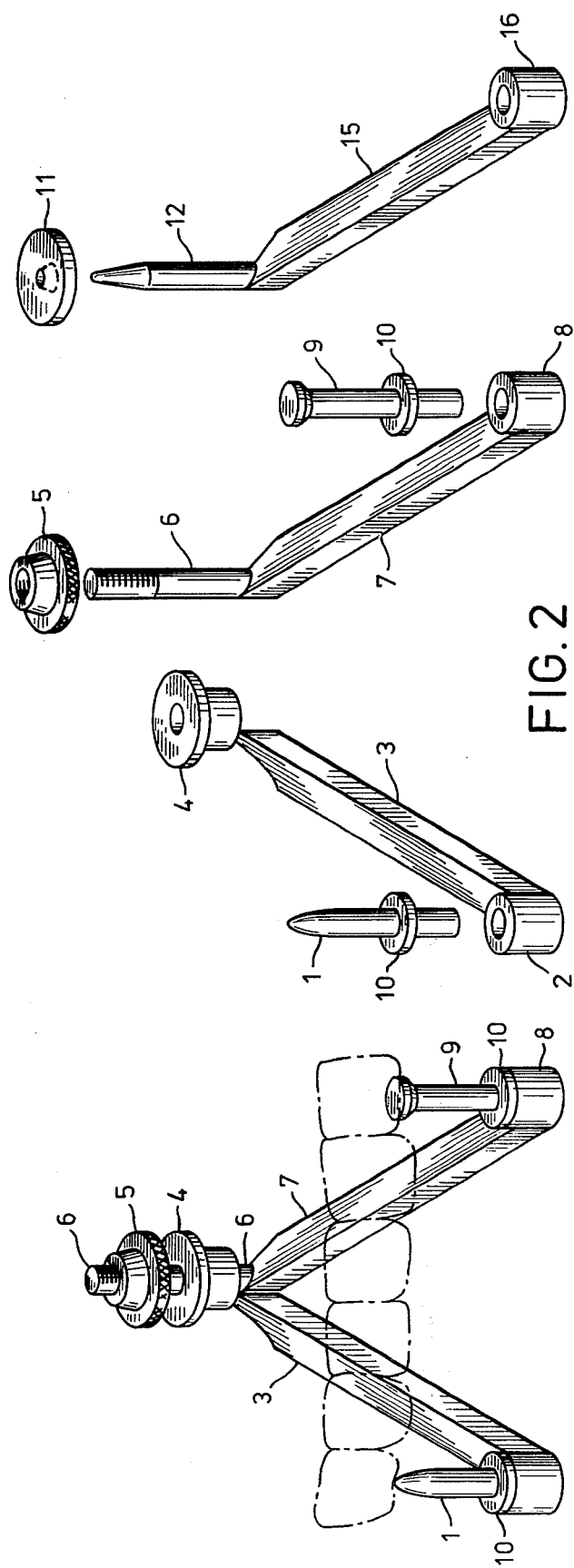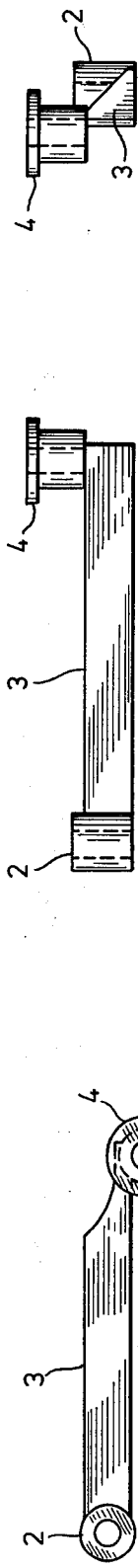

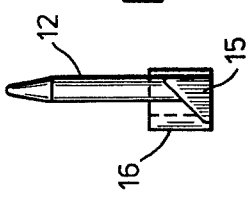
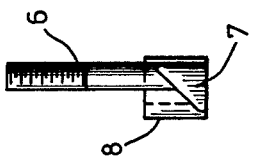
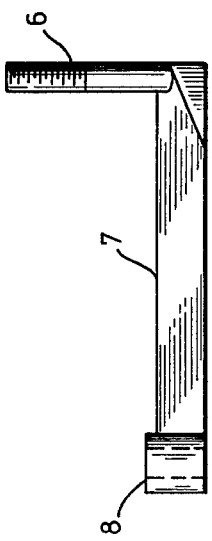
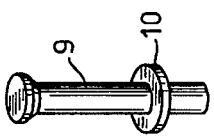
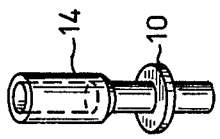

4,136,449

ADJUSTABLE DENTAL BRIDGE FIRING STAND

SUMMARY OF THE INVENTION

As Dental Laboratory Technicians we found a need for a sturdy, adjustable dental bridge stand because those available on the market did not meet our needs. We needed a bridge stand that was adjustable not only in length to hold various bridges, but also one that could accommodate varying tooth shapes and tooth conditions. Another problem we found in other bridge stands was that they were not sturdy, causing the bridge framework to wobble and fall from the stand when the stand was handled.

We feel that with the development of our "Adjustable Bridge Firing Stand" that these problems have been eliminated. Our adjustable bridge stand can open by means of a hinge design to enable it to hold all dental bridge frameworks at any of their tooth abutements. This adjustable bridge stand opens from zero degrees to 135 degrees, according to need, and at all conceiveable opening distances is completely sturdy. The sturdiness of this bridge stand comes from its over all design.

The supportive end posts have each been designed differently at their top end. These four designs used in any combination will hold any and all combinations of tooth abutements found in any and all dental bridge frameworks.

The unique design of the point of pickup prevents the bridge from tipping frontward, backward or to either side. These features, along with the basic design of the stand, make an extremely sturdy and functional bridge stand.

This dental bridge stand can be made out of a non-porcelain containing alloy or a standard ceramic support tray material, or any material that will not contaminate dental porcelains.

BRIEF DESCRIPTION OF THE DRAWINGS

FIG. 1 shows the Adjustable Dental Bridge Firing Stand assembled and ready for use.

FIG. 2 shows the bridge stand broken down into its component parts.

FIG. 3 shows an "alternate" design of the Parts 6 (End Pivot Post), 7 (The Stationary Base), and 8 (End Receptacle Base) shown in FIG. 2 when the bridge stand is to be made of an non-metallic material.

FIG. 4 shows a top view of Parts 2 (End Receptacle Base), 3 (Moveable Base), and 4 (The Pivot) and their arrangement and connections.

FIG. 5 shows a side view of Parts 2 (End Receptacle Base), 3 (Moveable Base), and 4 (The Pivot).

FIG. 6 shows an end view of Parts 2 (End Receptacle Base), 3 (Moveable Base), and 4 (The Pivot).

FIG. 7 shows the top view of Parts 6 (End Pivot Post), 7 (The Stationary Base), and 8 (End Receptacle Base) and their arrangements and connections.

FIG. 8 shows a side view of Parts 6 (End Pivot Post), 7 (The Stationary Base), and 8 (End Receptacle Base).

FIG. 9 shows an end view of Parts 6 (Threaded End Pivot Post), 7 (Stationary Base), and 8 (End Receptacle Base).

FIG. 10 shows an end view of the alternate design to the one shown in FIG. 3, Sheet 1.

FIG. 11 shows the side and top view of Part 5 (The Threaded Stabilizer Cap).

FIGS. 12 through 15 show the side views of the different designed Supportive End Posts. Part 1 (Standard Supportive End Post), Part 9 (Flat Supportive End Post), Part 13 (Pointed Supportive End Post), Part 14 (Hollow Supportive End Post), with the top view of the post shown above the side view.

FIG. 16 shows the side and top view of alternate Parts 11 (Stabilizer Cap) and 12 (Alternate Pivot Post) shown in FIG. 3, on Sheet 1.

DETAILED DESCRIPTION OF DRAWINGS

The following description describes Parts 1 through 16, as found in FIGS. 1 through 16 on the enclosed four sheets of drawings FIG. 2 shows the Adjustable Bridge Firing Stand broken into its five basic component pieces. It also shows and numbers the ten basic parts and how they relate and where they are connected. As can be seen in FIG. 2, Parts 2 (End Receptable Base), 3 (The Moveable Base), and 4 (The Pivot) are permanently connected together and Parts 6 (End Pivot Post), 7 (The Stationary Base), and 8 (End Receptacle Base) are permanently connected together.

The following description will list each part of the bridge stand, the name we have given the parts, its relative function and its dimensions. We feel these names and dimensions are the most appropriate.

Part 1: FIG. 2, Sheet 1 and FIG. 12, Sheet 2, is a Standard Supportive End Post. It's top end holds one abutement of the dental bridge up clear so the dental bridge will not touch any object that may contaminate it while it is being moved to or fired in the porcelain firing oven. The Supportive End Post has the following dimensions: Height: 0.6875 inches; Diameter: 0.0937 inches, Starts to taper from top. The taper length is 0.2812 inches from top, it's end is one of four different designs we have created for the ends of the supportive end posts, giving the dental technician the choice to use a design that would be most effective in holding sturdy the type of dental bridge he is working with. The Supportive End Posts are made to fit either End Receptacle Bases (Parts 2 or 8).

Parts 10: FIG. 2, Sheet 1 and FIGS. 12–15, Sheet 2 are permanently attached Support Post Stops to the Supportive End Posts. Parts 10 are found on all Supportive End Posts, (Parts 1, 9, 13 and 14) and their function is to keep the Supportive End Posts from falling through the open ended End Receptacle Bases (Part 2 and 8). They also give the Supportive End Posts stability and balance. Their dimensions are: Diameter; 0.1875 inches, Height; 0.0312 inches and it is positioned 0.4375 inches from the top of the Supportive End Posts.

Part 2: FIG 2 Sheet 1 and FIG. 5 Sheet 1 an End Receptacle Base holds any one of the four types of Supportive End Posts and is designed to be one of the two holders of the Supportive End Posts. It is permanently connected to the Moveable Base (Part 3). It's dimensions are: Height; 0.25 inches, Diameter; 0.1875 inches, Diameter of Center Hole 0.1094 inches and it goes completely through.

Part 3: FIG. 2, Sheet 1 and FIG. 4, Sheet 1, The Moveable Base permanently connects the End Receptable Base (Part 2) with the Pivot (Part 4). The triangular shape of the Movable Base gives the bridge stand stability and balance. It's dimensions are: Length; 1.25 inches, Base Width; 0.1875 inches, meeting in a top ridge because the Base is shaped in a Right Triangle. The Base is hollow with a thickness of 0.0625 inches for its walls.

Part 4: FIG. 2, Sheet 1 and FIG. 5, Sheet 1, The Pivot is one of two parts that form the hinge mechanism which allows the bridge stand to open and close making possible for any adjustment as needed. The Pivot (Part 4) is permanently connected to the Moveable Base (Part 3). The top of the Pivot (Part 4) is structured with a wide flat plate to act as one half of a stabilizer designed to keep the bridge stand from tipping forward, backward, or to either side while it is being moved. Dental tongs, which pick up the bridge stand by grasping a section of the End Pivot Post (Part 6), is inserted between the top plate of the Pivot (Part 4) and the lower plate of the Stabilizer Cap (Part 5), to pick up and move the whole bridge stand. Having the two flat plates of Parts 4 and 5 against the ends of the dental tongs keeps the bridge stand, as mentioned before, from tipping in any direction. This unique feature eliminates "Instability", one of the frequent problems now exsisting in other bridge stands. The Pivots dimensions are: Total height; 0.25 inches. Lower Cylinder height; 0.1875 inches with a diameter of 0.1875 inches with a center hole diameter of 0.1094 inches. The Upper cylinder plate height is 0.0625 inches with a diameter of 0.3125 inches and a center hole of 0.1094 inches.

Part 5: FIG. 2, Sheet 1 and FIG. 11 Sheet 2, The Threaded Stabilizer Cap, has a large flat plate at its base for stability. It is threaded on the Pivot Post (Part 6) and adjusted to a height close enough to Part 4's (the Pivot) top plate as to allow just enough room for the insertion of the dental tongs. The two flat plates press against the tongs to prevent backward or forward or sideways movement of the bridge stand while it is being transported to the porcelain firing oven. The Threaded Stabilizer Cap's dimensions are: Total Height; 0.125 inches. Large cylinder height 0.0625 inches with a diameter of 0.3125 inches and center hole of 0.0937 inches threaded (three thirty seconds threads) Small cylinder height is 0.0625 inches with a diameter 0.1562 inches and a 0.0937 inch center hole threaded (three thirty seconds threads).

Part 6: FIG. 2, Sheet 1 and FIG. 8 Sheet 2, The Threaded End Pivot Post fits through the Pivot (Part 4) and is the post upon which the Pivot (Part 4) moves giving the hinge affect to the bridge stand. A predetermined part of this threaded end post (the height of the end of the dental tongs) serves as the pick up point, by the dental tongs, at which the bridge stand is lifted and/or moved. The dimensions of the Threaded End Pivot Post are: Height, 0.6875 inches, Diameter; 0.0937 inches. This Pivot Post is threaded 0.1875 inches from the top with a three thirty seconds thread.

Part 7: FIG. 2, Sheet 1 and FIG. 7 Sheet 2 The Stationary Base permanently connects the Threaded End Pivot Post (Part 6) with the End Receptacle Base (Part 8). Part 7 is the counterpart of the Moveable Base (Part 3), both forming two sides of a triangle, thus giving the bridge stand complete stability. The Stationary Base's dimensions are: Length; 0.125 inches; Base of 0.1875 inches going to a ridge for its design is a right triangle. The Base is hollow with a thickness of 0.0625 inches for its walls. There is a 45 degree angle cut from the (Part 7) Stationary Base at the end with (Part 6) Threaded End Pivot Post. This allows the Moveable Base (Part 7) to open and lock at 135 degrees in conjunction with (Part 3) The Stationary Base. See FIG. 7 Sheet 3.

Part 8: FIG. 2, Sheet 1 and FIG. 8 Sheet 2, The second End Receptacle Base is the same as Part 2 (The First End Receptacle Base) having the same dimensions as Part 2 and being used for the same purpose. It is permanently connected to the Stationary Base (Part 7). It's dimensions are: Height, 0.25 inches; Diameter, 0.1875 inches; Diameter of Center Hole, 0.1094 inches and this hole goes completely through.

Part 9: FIG. 14, Sheet 2 and FIG. 2, Sheet 1, the Flat Supportive End Post has the same dimensions and function as the Standard Supportive End Post (Part 1) except for its top base which has been designed flat to hold large posterior abutements. As with the Standard Supportive End Post (Part 1) the Flat Supportive End Post (Part 9) has a permanently connected Support Post Stop (Part 10) to give it stability. The top end of the Flat Supportive End Post has the dimensions of: Total Height; 0.6875 inches; Lower Post diameter; 0.0937 inches; Small radius height; 0.0469 inches to a top diameter of 0.1562 inches.

Part 10: FIGS. 12-15 Sheet 2, Previously described on page 3 for the detailed description.

Part 11: FIGS. 3 and 16, Sheets 1 and 2 and FIG. 16 Sheet 2 respectively, the Unthreaded Stabilizer Cap is an "alternate" to the Threaded Stabilizer Cap (Part 5) but it is not threaded. This stabilizer cap has a centered, tapered hole which allows the cap to drop down to a predetermined point (the height of the end of a dental tong) on the unthreaded Pivot Post (Part 12) and there the cap will seat itself and become stable. Part 11, the Unthreaded Stabilizer Cap now functions the same as Part 5 (the Threaded Stabilizer Cap). The dimensions of the Unthreaded Stabilizer Cap are: Diameter, 0.3125 inches; Height, 0.125 inches and an Unthreaded center hole top of 0.0469 inches and a lower hole diameter of 0.0937 inches.

Part 12: FIG. 3, Sheet 1 and FIG. 10, Sheet 2, the Alternate Unthreaded Pivot Post is designed with an unthreaded end which is tapered so as to permit the Unthreaded Stabilizer Cap (Part 11) to fall down on it to a predetermined point so that it now acts as the Threaded Stabilizer Cap functions as previously described. It's dimensions are: Total Height, 0.6875 inches; Lower post diameter, 0.0937 inches with a "taper" from the top of a rounded radius 0.0312 inches in diameter down 0.1875 inches to the standard diameter of 0.0937 inches.

Part 13: FIG. 13, Sheet 2, the Pointed Supportive End Post has the same function and dimensions as the Standard Supportive End Post (Part 1) and the Flat Supportive End Post (Part 9) except for the top end design which tapers to a thin point so it can hold a narrow abutement crown. It, like the other Supportive End Posts has a Support Post Stop (Part 10) permanently connected to it. Its dimensions are: Total Height, 0.6875 inches; Diameter, 0.0937 inches and starts to taper to a sharp top point at 0.25 inches from the base.

Part 14: FIG. 15, Sheet 2, The Hollow Supportive End Post functions the same as the other previously described Supportive End Posts except for the top end which has been designed hollow. This is to hold an abutement that has an endodonic post extending from its bottom surface. It also has a Support Post Stop (Part 10) permanently attached to it and it's dimensions are: Total Height, 0.6875 inches; Lower Diameter is 0.0937 inches; It starts to widen 0.375 inches from the base to a 0.2187 inches diameter with a center hole diameter 0.0937 inches and the center hole depth is 0.25 inches.

Part 15: FIG. 3, Sheet 1, The Alternate Stationary Base functions the same and has the "same dimensions" as the Stationary Base (Part 7). The Alternate Stationary Base is a part of the alternate design shown in FIG. 3, Sheet 1.

Part 16: FIG. 3, Sheet 1, the Alternate End Receptacle Base functions and has the same dimensions as the End Receptacle Bases (Parts 2 and 8) but is part of the Alternate design given in FIG. 3, Sheet 1.

Note 1: Parts 1, 9, 13, and 14 (Supportive End Posts) have the same base diameter and attached Support Post Stops (Part 10) so they are interchangeable to fit either End Receptacle Bases (Part 2 or 8) as needed. They can be used concurrently or in any combination. Two of the same type of Supportive End Posts can be used at the same time in the bridge stand. The Supportive End Posts do not have to be removeable but could be a permanent part of the bridge stand if so wanted.

Note 2: Part 2 and Part 8 (End Receptacle Bases) are designed, shaped and have the same dimensions as each other allowing for the interchangability of the four types of Supportive End Posts (Parts 1, 9, 13, and 14).

Note 3: The "Alternate" design shown in FIG. 3 on Sheet 1 is given because it shows the changes needed in one side of the bridge stand when it is made out of any material other than metal. It lacks threads on the End Pivot Post (Part 12) and in the Stabilizer Cap (Part 11) because other materials do not lend themselves to being threaded.

Note 4: The bridge stand with the "Threaded" parts is to be made of an alloy that is not porcelain contaminating.

We claim:

1. An adjustable dental bridge firing stand for holding dental bridge framework, comprising in combination:

a first elongate member having a pivot post fixedly attached to one longitudinal end thereof and a receptacle having an aperture therein fixedly attached to the opposite end thereof;

a second elongate member having a first receptacle fixedly attached at one longitudinal end thereof having an aperture therethrough for receiving and rotatably holding said pivot post of said first elongate member with said first receptacle having a flat upper surface, and a second receptacle having an aperture therein fixedly attached to the opposite end of said second elongate member;

a securing member having a flat lower surface and an aperture therethrough for securing on said pivot post of said first elongate member above said first receptacle of said second elongate member; and a pair of support pegs for attachment respectively in said receptacle of the first elongate member and in said second receptacle of the second elongate member whereby said stand is adjustable to hold all sizes, shapes, and types of dental bridge frameworks during the various stages of firing.

2. An adjustable dental bridge firing stand as set forth in claim 1, wherein said pivot post has a threaded upper end and said securing member has cooperating threads within the aperture therein, so as to provide for predetermined adjustment of the space between the upper flat surface of the first receptacle and the flat lower surface of said securing member.

3. An adjustable dental bridge firing stand as set forth in claim 1, wherein said pivot post has a tapered upper end and said securing member has a correspondingly tapered aperture therethrough to provide for securing said securing member a predetermined distance from the flat upper surface of the first receptacle.

4. An adjustable dental bridge firing stand as set forth in claim 1, wherein said stand is constructed of metal alloy which is nonporcelain contaminating.

* * * * *